United States Patent [19]
Stokes et al.

[11] Patent Number: 5,814,089
[45] Date of Patent: Sep. 29, 1998

[54] LEADLESS MULTISITE IMPLANTABLE STIMULUS AND DIAGNOSTIC SYSTEM

[75] Inventors: Kenneth B. Stokes, Anoka; Adrianus P. Donders, Andover, both of Minn.

[73] Assignee: Medtronic, Inc., Minneapolis, Minn.

[21] Appl. No.: 768,384

[22] Filed: Dec. 18, 1996

[51] Int. Cl.⁶ .................................................. A61N 1/368
[52] U.S. Cl. ................................ 607/32; 607/33; 607/60
[58] Field of Search ............................ 607/10, 16, 17, 607/30, 33, 60, 32

[56] References Cited

U.S. PATENT DOCUMENTS

| | | | |
|---|---|---|---|
| 3,824,129 | 7/1974 | Fagan, Jr. | 607/33 |
| 3,942,535 | 3/1976 | Schulman | 607/33 |
| 3,943,936 | 3/1976 | Rasor et al. | 128/419 P |
| 4,134,408 | 1/1979 | Brownlee et al. | 607/33 |
| 4,166,470 | 9/1979 | Neumann | 607/33 |
| 4,245,640 | 1/1981 | Hunt | 128/419 B |
| 4,432,363 | 2/1984 | Kakegawa | 607/33 |
| 4,763,656 | 8/1988 | Nauman | 128/421 |
| 4,886,064 | 12/1989 | Stranberg | 128/419 PG |
| 4,987,897 | 1/1991 | Funke | 128/419 PG |
| 5,012,806 | 5/1991 | De Bellis | 128/419 P |
| 5,109,845 | 5/1992 | Yuuchi et al. | 128/421 |
| 5,314,457 | 5/1994 | Jeutter et al. | 607/116 |
| 5,324,316 | 6/1994 | Schulman et al. | 607/61 |
| 5,383,915 | 1/1995 | Adams | 607/60 |
| 5,405,367 | 4/1995 | Schulman | 607/61 |
| 5,411,535 | 5/1995 | Fujii et al. | 607/32 |
| 5,466,246 | 11/1995 | Silvian | 607/32 |
| 5,476,488 | 12/1995 | Morgan et al. | 607/30 |
| 5,487,760 | 1/1996 | Villafana | 607/33 |
| 5,630,835 | 5/1997 | Brownlee | 607/32 |
| 5,683,432 | 11/1997 | Goedeke et al. | 607/32 |

*Primary Examiner*—William E. Kamm
*Assistant Examiner*—Kennedy J. Schaetzle
*Attorney, Agent, or Firm*—Michael J. Jaro; Harold Patton

[57] ABSTRACT

There is provided an implantable system and method for delivering stimulus pulses and/or collecting data from a plurality of sites within a patient's body, having a main controller device with a power source, a stimulator/sensing devices at each of said sites, and circuitry for high frequency transmission of power from the main unit to each of the remote devices. Power is transferred by converting it into a high frequency at the controller unit, and periodically or on request transmitting it to the respective devices. The main controller unit and each respective device also preferably has one or more sensors for collecting data and processor circuitry for analyzing such data. Each remote device has a transmitter for transmitting collected data back to the main controller; the main controller has encoding circuitry for encoding a data component onto the high frequency carrier along with the power component. The controller unit and the respective devices are also equipped with circuitry for controlling power transmission on a need basis, i.e., when the remote device needs power and requests it. The system also performs a transmission parameter test, and adjusts parameters of the transmitted signal, such as frequency and amplitude, as may be indicated.

31 Claims, 7 Drawing Sheets

LEADLESS MULTISITE IMPLANTABLE STIMULUS AND DIAGNOSTIC SYSTEM

FIELD OF THE INVENTION

This invention relates to implantable medical systems for delivery of stimulation treatment and the like and, particularly, leadless systems having multiple stimulus and/or data collection sites.

BACKGROUND OF THE INVENTION

Implantable medical treatment systems have achieved great success and have come into widespread use in recent decades. For example, pacing systems, including implanted pacemakers, are widely used to treat various cardiac conditions by delivery of stimulus pulses to the heart. Another development is that of the implantable defibrillator, or pacemaker/cardioverter/defibrillator for delivering different types of shock therapy to a patient's heart, as well as pacing pulses. Other areas that are under development and are being explored include implantable diagnostic devices for collecting information concerning the activity of a patient's heart or other organ, and relay of collected data to an external programmer; and various neuro stimulation devices.

The development of increasingly sophisticated implantable medical systems has led to a desire for a greater system capability in terms of applying stimuli to different selected sites, or locations, as well as collecting data from different sites in order to control the manner of stimulation automatically or to transmit collected data to the physician for evaluation. The desire to expand implanted systems in order to treat plural sites creates a need for increased system flexibility, but without substantial increase of system cost. An important aspect of providing such multisite systems is that of simplifying the power requirements at each site. If plural sites are utilized but each site requires a special purpose lead connected to a common device for delivering stimulus pulses and/or collecting data, this may result in a complex system requiring extensive implant time, such that many physicians may not want to deal with it. Moreover, in implanted pacemaker systems, the long-term reliability for the lead or leads remains a potential problem, or "weak link" in the system. For example, a pacing lead is subject to about 38 million flexes per year, it is subject to the body's defense mechanisms, and is placed in an extremely hostile environment. The result is that conductors fracture, insulation degrades for various reasons, and the leads can become infected. As is known, removal of chronically implanted leads is extremely difficult. In addition, when two or more leads are involved, the problems are compounded. The more hardware there is implanted, the greater is the risk of thrombosis (embolism, thoracic outlet syndrome, SVC syndrome, etc.), infection, valvular, and other tissue damage, etc. Thus, in an ideal system such leads are eliminated entirely. However, a leadless plural site system where each site has an implanted device with its own battery source likewise has the problem of substantial additional expense attributable to the need of having a battery for each remote implanted device at each respective remote site.

The prior art provides examples of wireless data communication between two or more sites within a patient. For example, U.S. Pat. No. 5,411,535 discloses a pacer system where data is sent from a main pacer unit to remote electrode units, for controlling delivery of pace pulses as well as providing sensed data from the electrode units back to the main pacer. However, each remote location has its own battery supply. See also U.S. Pat. No. 5,405,367, which discloses multiple stimulators devices at different sites. Each of the implanted stimulator devices receives energy from an alternating magnetic field, i.e., through a transformer, from an external source. A transparent difficulty with this system is that it requires frequent if not substantially continuous transfer from an external source to the implanted devices, which would be an unacceptable arrangement in most cases. See also U.S. Pat. No. 4,886,064, which discloses sensor units separate from an implanted pacemaker unit, where the sensor units wirelessly transmit data to the pacemaker. However, each sensor unit has its own battery power source.

The prior art thus shows transformer-type coupling of energy from an external source to an implanted system, and wireless transmission of data between multiple implanted devices in a patient. What is desirable in order to expand system capability for treatment at multiple patient sites is a more flexible implantable system with devices at plural sites; a system that does not require multiple leads from the implantable stimulator to the respective plural sites; and a system that has the capability of transmitting power from a single battery source to the respective site devices on an efficient basis.

SUMMARY OF THE INVENTION

It is an overall object of this invention to provide an implantable leadless system for stimulating plural sites in a patient and/or collecting data from such sites for external transmission. As used herein, the term "leadless" refers to the absence of a lead interconnecting the plural sites, it being understood that one or more of the site devices of the system may have a lead for delivery of stimulus pulses and/or sensing data. The flexible system and method of this invention has the aim of providing a power source, e.g., a battery, in a central controller, and transmitting capability for transmitting power from the central controller to a remote device or to each of a plurality of remote site devices, the transmission being controlled in order to optimize power efficiency.

In accordance with the above object, there is provided an implantable system and method for pacing or otherwise treating a patient and/or for collecting data, the system having a controller unit and one or more site-specific devices separate from the controller unit, where the controller unit has a power source and a transmitter for transmitting to each remote device a high frequency signal comprising at least a power component derived from the power source. Each remote unit in the system has a receiver for receiving the high frequency signal and a circuit for deriving power from it, and a power supply for storing the derived power and powering the unit. Further, the system preferably has the capability of transmitting data from the main controller unit along with the power, with a power component and a data component being modulated onto a common carrier for transmission to one or more of the remote devices. Similarly, each remote device has a transmitter for transmitting sensed data back to the main controller unit.

In a further embodiment of the invention, the system comprises capability for controlling the high frequency power transmission as a function of the power requirements or demand at each remote unit. In this embodiment, each remote unit operates on a very low power basis except when system demand calls for it to deliver a treatment such as stimulus pulses, or to transmit sensed data back to the main controller unit.

DESCRIPTION OF THE PREFERRED EMBODIMENTS

Figure 1:
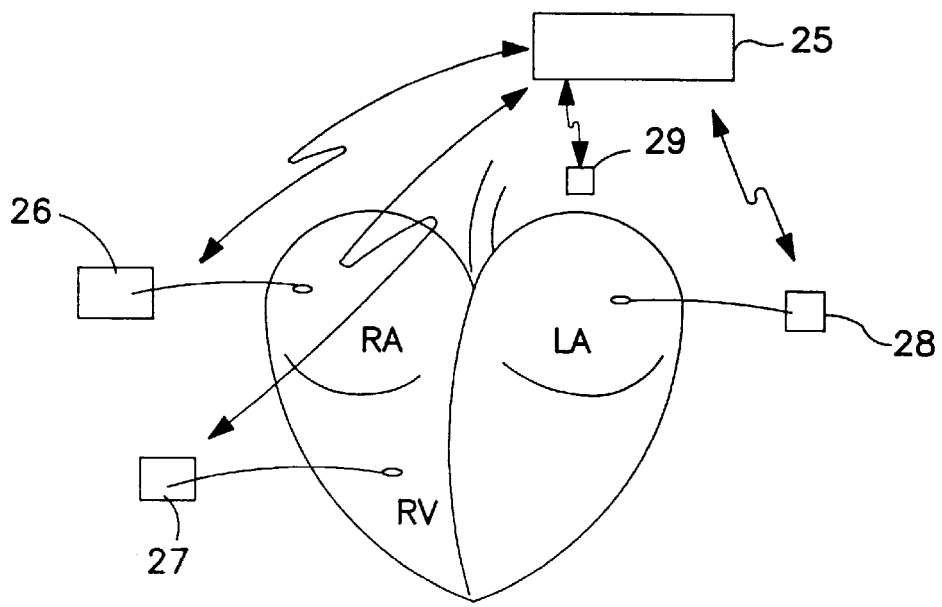
FIG. 1 is a schematic representation of an implanted plural site system in accordance with this invention.

Referring now to FIG. 1, there is shown a schematic diagram of a system in accordance with this invention. A main implantable controller unit 25 is illustrated, which provides transmission of power and data to each of remote units 26, 27, 28 and 29 as illustrated. Any number of remote units may be used within the scope of this invention. As illustrated, each remote unit is shown diagrammatically as producing a signal which is delivered to a target location, in this instance in or near the heart. Thus, unit 26 delivers pacing or cardioversion pulses to the right atrium; remote unit 27 delivers pacing or cardioversion pulses to the right ventricle; remote unit 28 delivers pacing or cardioversion pulses to the left atrium; and remote unit 29 delivers stimulus pulses to another location. For example, septal stimulation adjacent to the right ventricular outflow tract (RVOT) would capture the conduction system, which has value in providing better cardiac output due to a more natural contraction pattern, potentially useful for CHF. Stimulation can be directed to other areas near the RVOT, for treating HOCM by stimulating the septum to contract before the rest of the ventricle. Each of the remote devices may have one or more electrodes positioned on its case and may be positioned so that the electrodes are in contact with the target site. Alternately, one or more of the remote devices may have a lead for delivering stimulus pulses to a target site. As discussed further hereinbelow, each of units 25–29 is suitably provided with one or more sensors for detecting signals or other data from its environment, and there is two-way data transmission between controller 25 and each of the remote units 26–29.

Figure 3A:
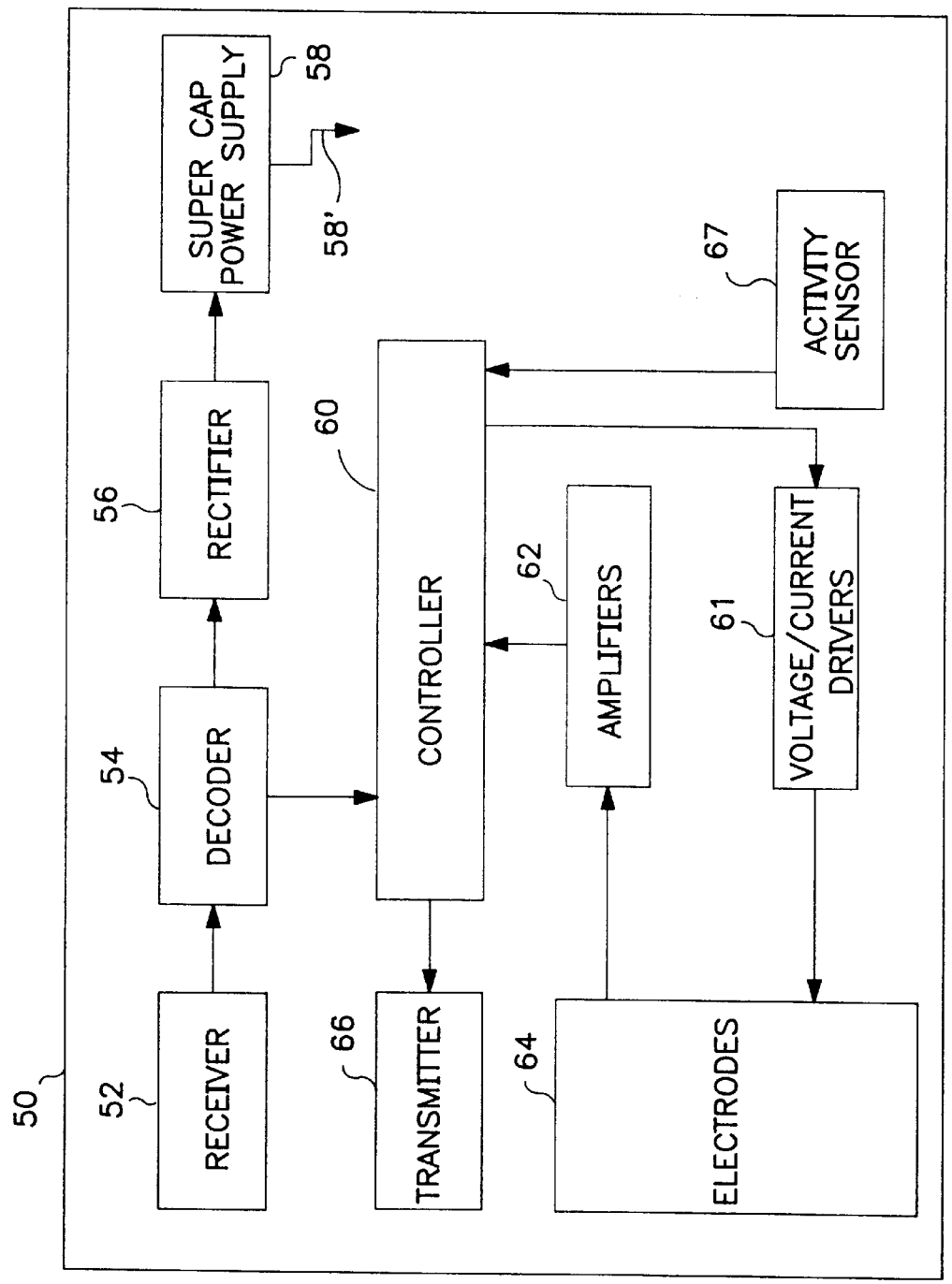
FIG. 3A is a block diagram of a stimulation and/or sensing device at a remote site.
Figure 3B:
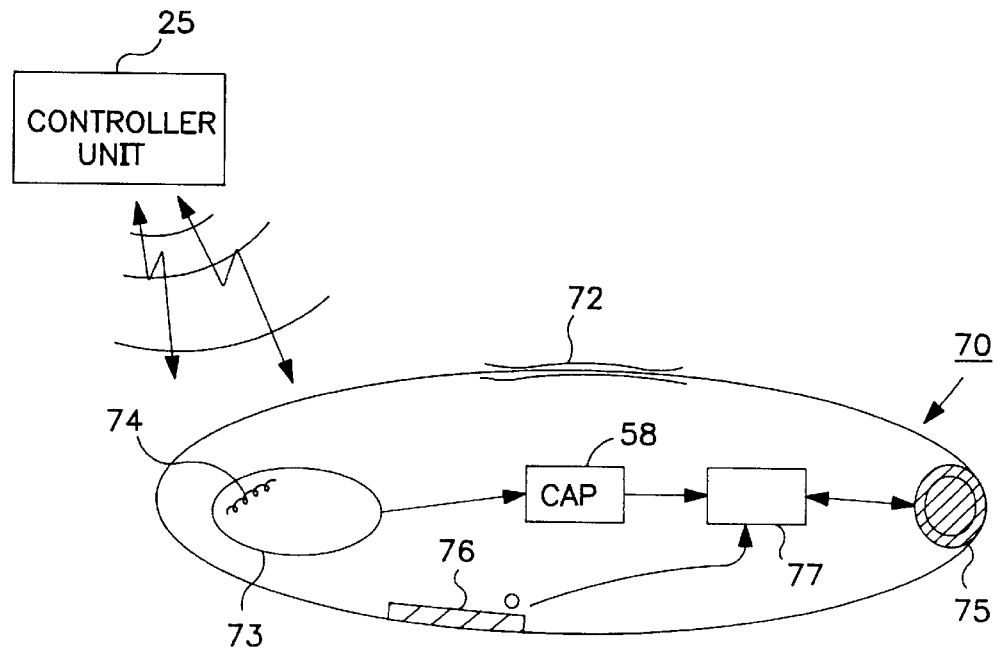
FIG. 3B is a simplified schematic of a remote device housed in a ceramic can which receives high frequency energy from the controller unit and provides stimulus pulses to a pacing electrode.

In practice, the remote devices such as depicted schematically in FIG. 3B are small enough to be implanted with an implant tool such as a catheter. The catheter suitably has a steerable tip or is under stylet control, and is inserted through a vein to the heart. The implant module, or unit, is floated in the distal end of the catheter, with the distal electrode exposed. After an appropriate location is found by the physician, e.g., by using typical parameters such as P-wave amplitudes in the atrium or ventricular thresholds, the implant module is fixed to the heart at the desired location. This is done by controlling means either on or in the catheter, the implant module, or both. For example, a tined module can simply be pushed or ejected out of the end of the catheter. A module can be provided with helical fixation means, and can be held in the catheter tip while the catheter is rotated to screw it into the myocardium, after which is it is released. In a known technique, a stylet attached to the implant module might be used to rotate it.

Figure 2B:
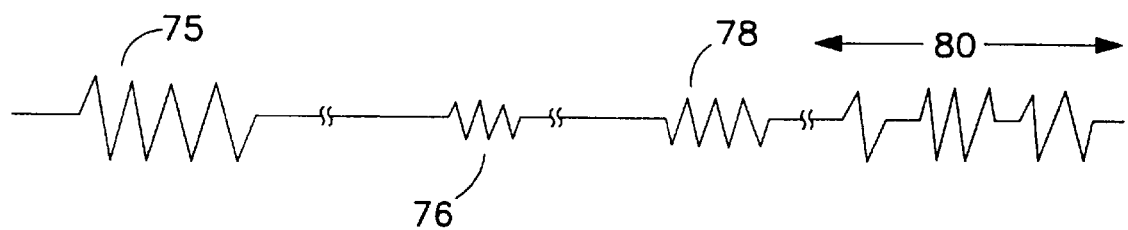
FIG. 2B is a time representation of a decoded power component and data component, which is transmitted on a high frequency carrier to one or more remote stimulators in accordance with this invention.
Figure 2A:
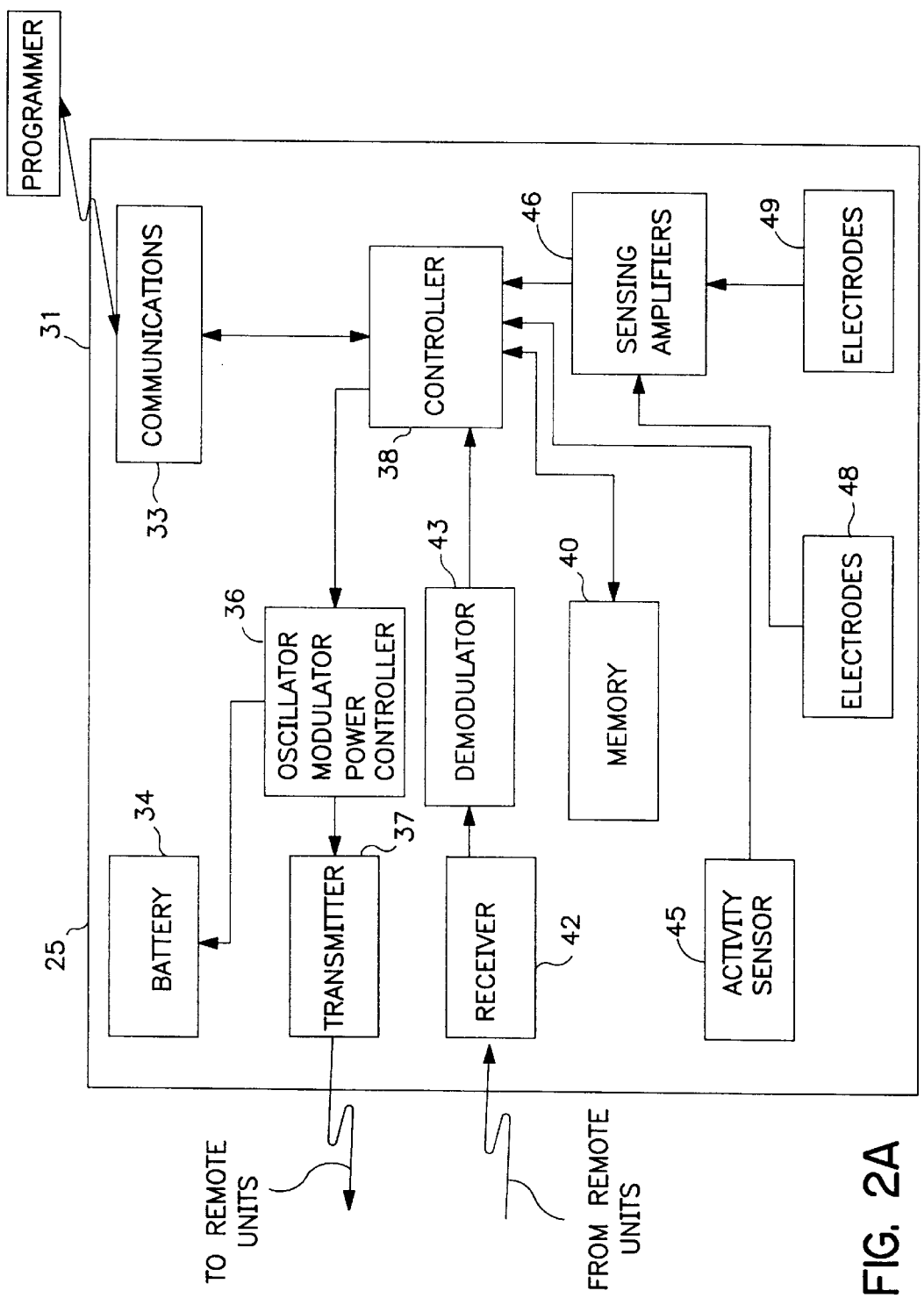
FIG. 2A is a block diagram of a controller unit in accordance with this invention which transmits power and data to a plurality of remote units.

Referring now to FIG. 2A, there is shown a schematic diagram of an implantable controller unit 25, which in the system and method of this invention provides power for transmission to each of the remote units. Implantable unit 25 is in two-way communications with an external programmer 31, through a communicator, or transmit/receive subsystem 33. Battery 34 is connected to all of the circuitry of unit 25, meaning that it provides power to each of the blocks illustrated, as is designated by lead 34'. The battery is shown connected directly to an oscillator/modulator/power converter 36 which performs dual functions. First, the power converter section receives power from the battery 34 and generates power wave forms, which modulate a carrier signal for carrying power. Further, the modulator portion 36 receives data signals from controller 38, and further modulates the carrier to carry such data signals for transmission to one or more of the remote devices. The output of the modulator/power converter circuit 36 is coupled to transmitter 37, which transmits a high frequency signal containing a power component and a data component. Controller 36 controls the transmission parameters, e.g., carrier frequency and amplitude, as discussed further below. The nature of the power and data wave form are discussed further in connection with FIG. 2B below.

The construction of the transmitter can be in accord with several approaches. A single point, omni-directional transmitting antenna, made of metal, can be used for high frequency transmission of the energy and data signals. Such an approach has the advantage that the antenna can transmit to plural remote devices and need not be directionally tuned, but requires relatively high energy. Another approach is to use transmitting and receiving antennas configured as primary and secondary transformer windings, oriented for directional transmission. Here, the efficiency depends upon the size of the antennae, and the distance between them, which is generally on the order of 5–8 cm, or several inches. For this directional arrangement, the transmission is substantially perpendicular to each antenna coil.

Controller unit 25 additionally has a receiver 42, for receiving high frequency communications from each of the remote devices which are part of the implanted system, e.g., devices 26–29 as shown in FIG. 1. The received signals are demodulated in demodulator circuit 43, the demodulated data then being coupled through to controller 38. Controller 38 preferably incorporates a microprocessor and other required timing circuits, for effecting control of modulator/power converter circuit 36. Controller 38 is also in two-way communication with memory 40, for storing data and for receiving algorithms as are called for, in a known fashion. Additionally connected to controller 38 is a sensor, illustrated as activity sensor 45, which provides input data concerning patient activity, in a manner well known in the pacing art. This data is processed by controller 38 and used for controlling the modulation carried out in block 36. Additionally, electrodes 48 and 49 are illustrated providing inputs to sensing amplifiers 46, the data from which is likewise coupled to controller 38. Electrodes 48, 49 may be housed either on the controller unit, or may be housed on leads extending from the controller unit; and, of course, such electrodes can be placed on one or more remote devices. The collected data may, as in a pacemaker system, provide signals representative of cardiac activity either for control use or for diagnostic use. Data inputted from sensor 45 and/or electrodes 48, 49 may be collected and transmitted through communicator block 33 to external programmer 31, for evaluation by a physician.

Referring now to FIG. 2B, there is shown a time diagram illustrating the nature of data encoded onto a high frequency carrier, which is transmitted from transmitter 37 to one or more external implanted devices. The carrier, not shown, is suitably a high frequency carrier. The transmitted waveform must be in a frequency range that allows efficient transmission within the body using small antennae; which transmits power sufficient to carry to the remote units, e.g., up to about 10 cm, while being low enough to be provided by the controller battery over a nominal implant lifetime; and the signal may not be damaging to body tissue or cause unwanted stimulus generation. The frequency is in a range of 30–250 MHZ; high frequencies around 250 MHZ are appropriate. The amplitude of the signal is adjustable, depending on the spacing of the remote units. The amplitude and frequency can be adjusted through controls from programmer 31; and in response to signal strength data sent back from the remote unit, as discussed further in connection with FIG. 4C. The parameters are interactive, being a function of antenna design, inter-unit geometry, and body conditions such as air in the lungs, liquid in the GI tract, etc. For this reason, the system and method include a transmission parameter test for adjusting frequency and amplitude in order to optimize transmission.

Still referring to FIG. 2B at 75 there is shown a constant asynchronous "trickle charge" signal, which is a power carrying signal used to charge up a special purpose capacitor provided in each remote device (see block 58, FIG. 3A). Following this in time sequence, there may optionally be a reset code as illustrated at 76, to communicate to the remote device that the trickle charge has been completed. Following this in time, at 78 there is delivered an identification code to communicate with one or more particular external devices. This feature is optional, and may be used to direct control data that has been generated at the controller or received from the external programmer, to selected one or more remote devices. Following this, the information or data signal is delivered, as illustrated at 80. This data may be encoded in any desired manner, and carries control data to instruct the remote stimulator or device as to its operation. The manner of encoding and demodulating the data is a matter of design choice, and may be done in any conventional manner. The power is transmitted between "events" such as stimulation, sensing data transmission from a remote unit, etc.

Referring now to FIG. 3A, there is shown a block diagram of a remote device 50, in accordance with this invention. A receiver circuit 52 is provided for receiving and filtering out the carrier signal which has been transmitted from the controller unit, which carrier signal carries both the power and data components. The received signal is decoded in circuit 54, and separated into power and data components. The decoded power component is coupled to rectifier 56, the output of which is a DC voltage which is coupled to a large capacitor, or "SUPER CAP" which is part of power supply 58 for the remote unit. Cap 58 can have a value of about 0.3 F, and yet be physically quite small. Such a capacitance value is large enough to power the device for pacing for several weeks before needing a trickle recharge, by using modem low threshold, high impedance electrodes. Power supply 58 provides power to all circuitry of the device, as indicated by arrow 58'. Returning to decode block 54, the data component of the received signal is coupled to controller 60, which suitably comprises a microprocessor or equivalent logic and associated memory. Controller 60 is used to control the activities of the remote device, which include delivering stimulus pulses through driver 61 and electrodes 64, and receiving sensed information picked up at electrodes 64 and amplified at 62. These procedures and circuits are well known in the art. Also, as illustrated, an activity sensor 67 or a plurality of sensors provide data inputs to controller 60. This data can be stored for transmission back to the main controller unit, and/or can be used internally for control of the remote device. Controller 60 outputs data through transmitter 66 to controller unit 25. Block 60 includes a suitable high frequency carrier oscillator and modulator. The transmitted data may be sensed data, e.g., data representative of cardiac events for processing at the controller unit; or, as discussed further in connection with FIG. 4, it may involve request signals for controlling the transmission of power back to the remote device. It is to be understood that the processing of sensed information may be divided between the main controller unit 25 and each of the remote units 50, and that such division is a matter of design choice. Thus, at the time of implant, the assignment of processing tasks may be made through programmer 31, and relayed by transmission of data to each of the remote units. Of course, the controller unit 25 receives data from each of the remote units, and accordingly can process all of this data to make global control decisions.

Referring now to FIG. 3B, there is shown a simplified schematic of an implanted device or module 70 which receives high frequency power from controller unit 25. The implantable device has a housing in the form of a ceramic can 72, which permits efficient penetration of the high frequency signal for reception by the receiver and power supply circuitry which is illustrated at 73. The receiver includes a micro antenna, illustrated schematically at 74. This schematic illustrates flow of power internal to this device from the receiver through to cap 58, and in turn through output circuitry 77 to a pacing button, or surface electrode 75 which is positioned on the ceramic can. The use of one or more surface pacing electrodes 75 in this manner enables implantation and positioning of devices to deliver the desired treatment signals without the use of a lead, as discussed above. A miniature accelerometer 76 is placed within the module, e.g., on the ceramic substrate, to provide capture detection signals.

Figure 3C:
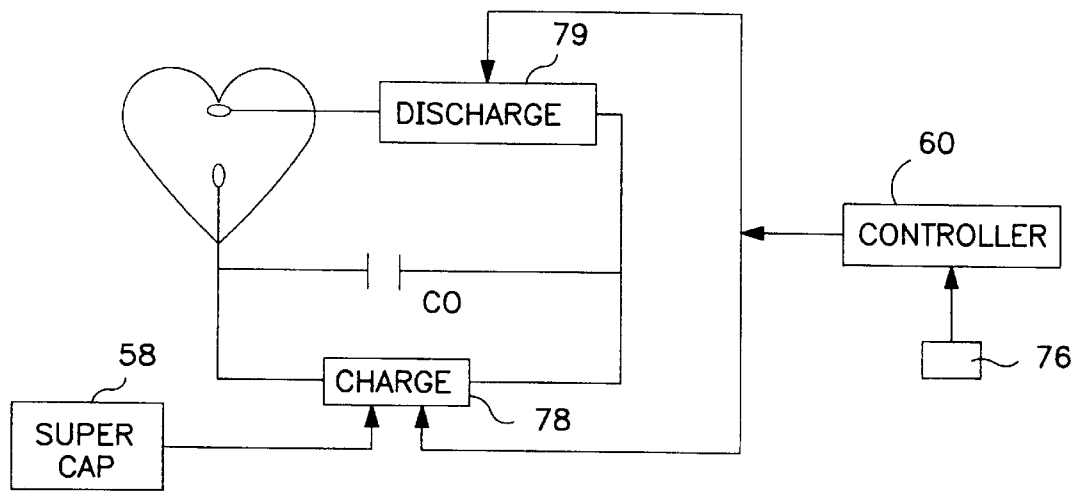
FIG. 3C is a simplified circuit diagram showing charging and discharging of an output capacitor for delivering stimulus pulses to a patient's heart from a remote device.

Referring now to FIG. 3C, there is shown a simplified schematic diagram of output circuitry by which stimulus pulses are delivered to a target site, such as the patient's heart. The SUPER CAP 58 delivers energy through a switchable charge circuit 78, which in turn is controlled by controller 60. When the charge circuit is switched to a charge position, power from CAP 58 is delivered across output capacitor $C_o$. When the capacitor is charged, and it is time to deliver a stimulus pulse to the heart, controller 60 switches discharge circuit 79 to provide a circuit path through the heart, thereby delivering the stimulus pulse in a known and conventional manner. Accelerometer 76 is shown providing input signals to controller 60, for purposes of capture detection. Signals generated by the accelerometer as a result of heart wall motion are used to inform the controller 60 that a contraction has occurred, thus providing capture detection without requiring sophisticated electronics and associated problems such as electrode polarization.

Figure 4A:
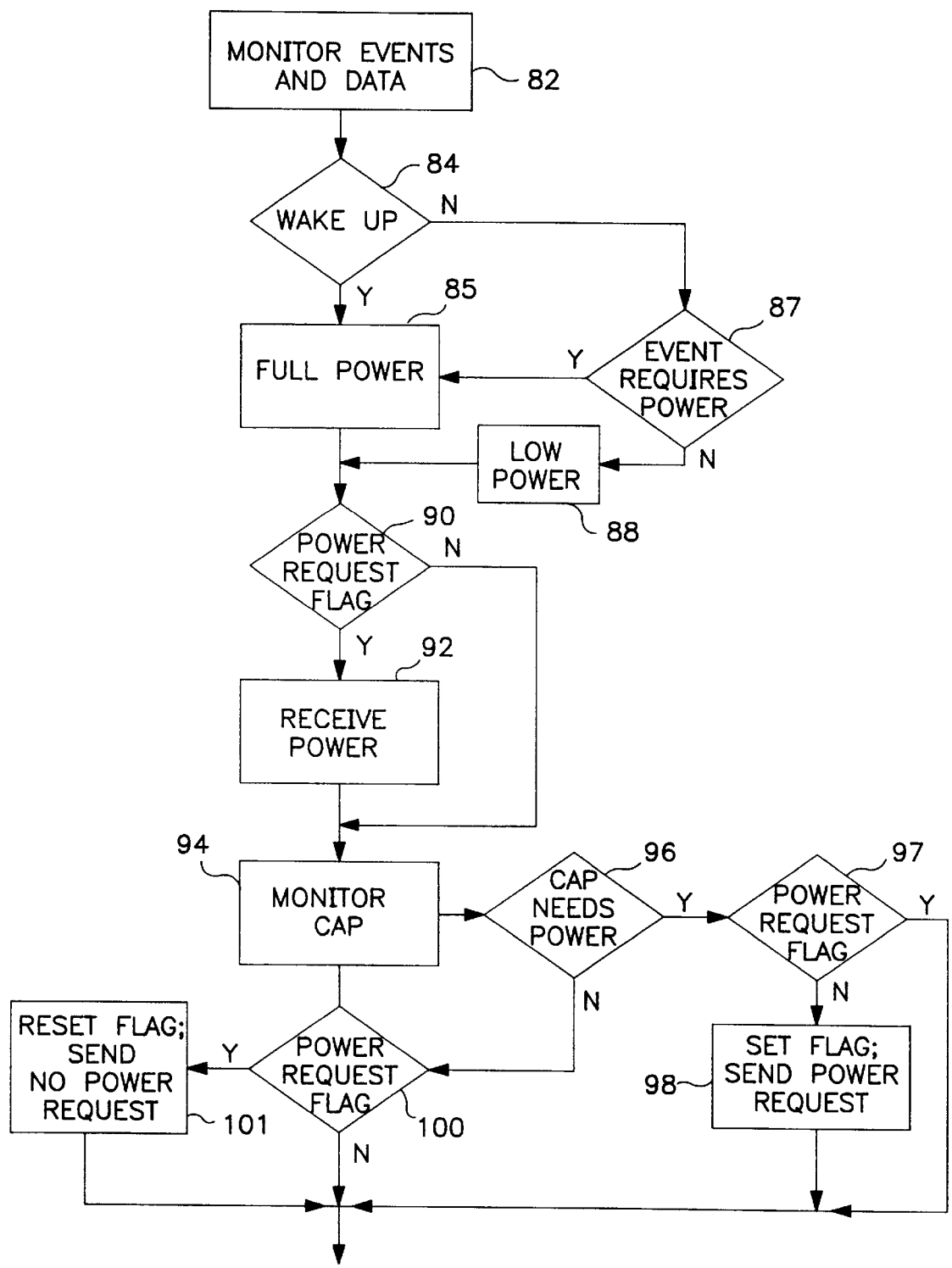
FIG. 4A is a flow diagram showing the primary steps in the method of this invention whereby a remote device requests power from the controller and maintains itself in a low power mode except when required to be active.
Figure 4B:
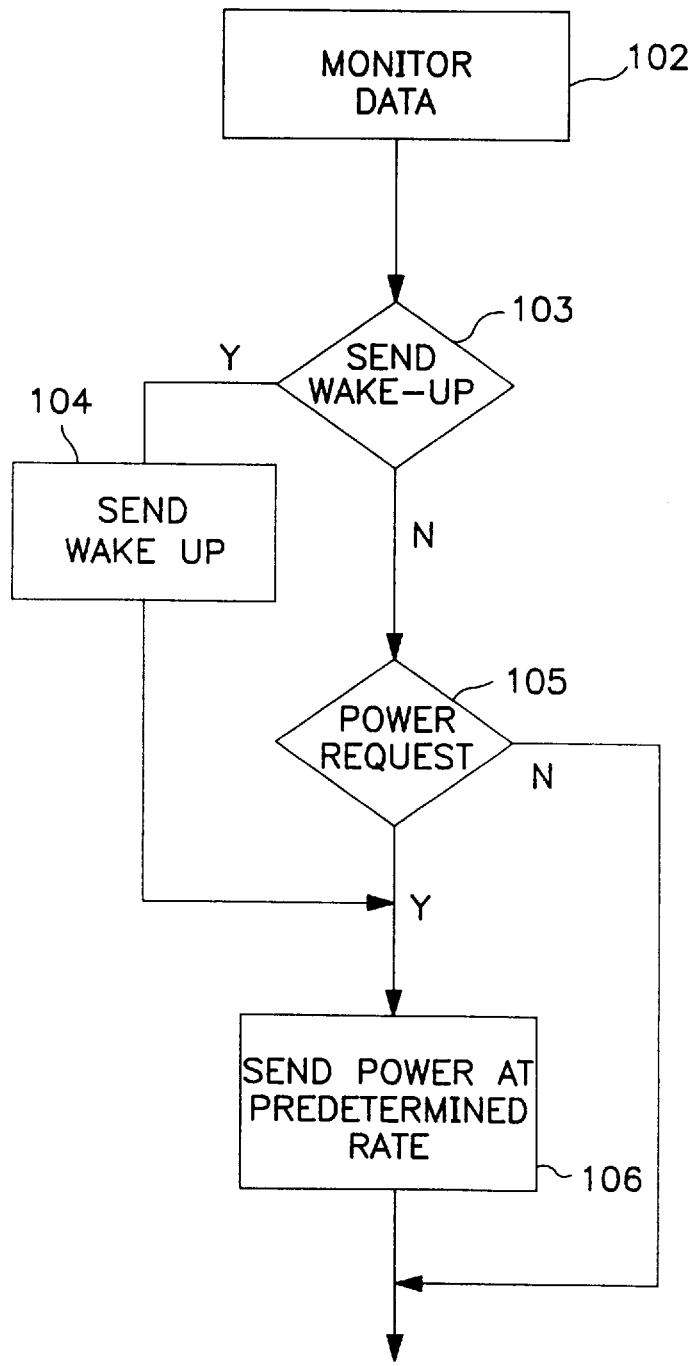
FIG. 4B is a simplified flow diagram showing the steps at the controller unit taken to deliver power on request.

Referring now to FIGS. 4A and 4B, there are shown simplified flow diagrams illustrating the method of this invention for providing power to one or more of the remote units "on request," i.e., when and as the remote unit signals that it needs power. The routine of FIG. 4A, which represents steps taken in the remote device, may be run periodically, at any desired interval. At the start of the routine, events and data received from controller 25 are monitored at 82. Such events may be detection of cardiac P or QRS waves, a cardiac arrhythmia, etc. At 84, it is determined whether there has been a wake-up command from the main controller. If yes, the routine immediately goes to 85 and sets the remote device in full power mode. If no, the routine goes to 87 and determines whether an event has been detected that requires power. If yes, the routine branches to 85 and goes into full power mode, but if no, it goes to 88 and goes into low power mode. Following this, at 90 it is determined whether the power request flag is presently set. If yes, at 92 the device waits until a power signal has been received, and then goes to 94 to monitor the capacitor. If the power request flag is not on, the routine goes directly from 90 to 94 and monitors the cap. Following monitoring of the charge on the capacitor, at 96 it is determined whether the capacitor needs additional power. If yes, the routine goes to 97 and determines whether the power request flag is already set. If yes, the routine exits; if no, at 98 the flag is set, and a power request signal is transmitted to the main controller. Returning to 96, if the cap does not need power, the routine goes to 100 and determines whether the power request flag is set. If no, the routine exits; if yes, at 101 the flag is reset, and a no power request is sent to the main controller.

Referring now to FIG. 4B, there is shown a simplified flow diagram of steps taken at the main controller unit, to regulate transfer of power to one or more remote units. At 102, data that has been collected and stored in memory 40 of controller 25 is analyzed, and at 103 a decision is made as to whether to send a wake-up call to a unit, to make sure it is in a full power mode. Such a wake-up call may be initiated, for example, by a decision to have a remote pacemaker unit go through a threshold test, or by a decision that regular pacing activity should be resumed because of monitored data or received programmer information. If a wake-up call is to be sent, the routine branches to block 104, and sends a wake-up call to a designated remote unit; then at block 106 controller 38 controls unit 25 to send power to the unit. If no wake-up call is to be sent, the routine goes to block 105 and determines whether there has been a power request from a remote device. Of course, if there is more than one remote device, as in the preferred embodiment of this invention, a determination is made with respect to each such remote device. If there has been a power request, the routine goes to 106 and sends power in the normal manner. If there has been no power request flag, the routine exits.

Figure 4C:
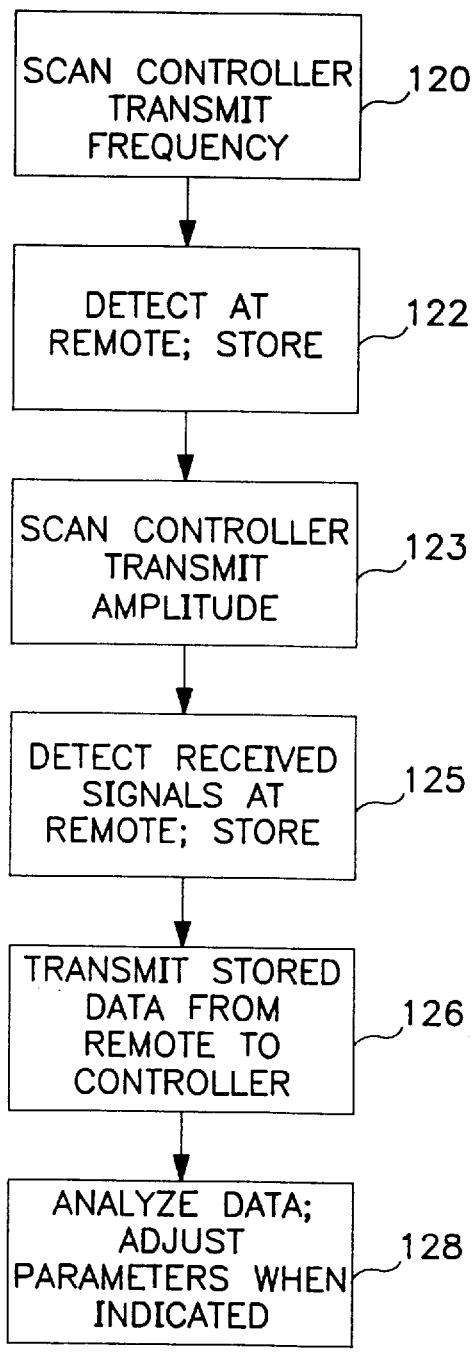
FIG. 4C is a flow diagram showing steps for adjusting transmission signal parameters.

Referring now to FIG. 4C, there is shown a flow diagram of the primary steps taken in performing a test to determine whether there should be any parameter adjustment of the signal transmitted from controller 25 to one or more remote devices. As discussed above, the frequency and amplitude parameters are affected by conditions in the body, such that they should adjusted at time of implant and subsequently. The routine of FIG. 4C shows a technique for determining at the remote site the effect of changing parameters, and providing feedback to the main controller for a determination of whether an adjustment can be made to improve efficiency. The program can be initiated by a command from an external programmer, or can be automatically initiated by the implanted system, e.g., once a week or at any other desired interval.

At step 120, the routine scans the controller transmit frequency through a predetermined range, e.g., delivers power signals carrying a trickle charge 75 as seen in FIG. 2B with a first frequency n times, then increments the frequency and delivers the next n transmissions, etc. Suitably an identification or sync pulse is transmitted between power transmissions, to indicate frequency steps during the scan. When the respective signals are received at remote device 50, signals are generated at decoder 54 representing the level of the received power signal, and these levels along with the identification or sync data are stored in controller 60, as indicated at 122. After the frequency scan, at 123 the controller goes through a scan of signal amplitude, and again, as indicated at 125, the decoder detects the received signals and stores representations of the power levels associated with the different amplitude transmissions. Following the two scans, at 126 the remote device transmits the stored data back to the controller. At 128, the main controller analyzes the data, and determines therefrom whether an adjustment of frequency or amplitude is indicated, so as to improve efficiency of power transmission. For example, the data may indicate that a certain frequency shift results in a relatively significant increase in received power without any increase in transmitted power; while an increase in transmitted power due to an amplitude increase does not provide a proportionate increase in received power. By performing this test at the time of system implant, the transmitter parameters can be initially adjusted for efficient operation. By subsequently performing the test periodically, the parameters are tuned to adapt to changed body circumstances so as to maintain optimally efficient transmission. Such transmitter adjustment, along with the above-described technique of providing power to each remote device upon request, enables efficient power transfer to each remote device.

We claim:

1. An implantable stimulating system for stimulating a patient, said system comprising:

at least one implantable stimulating unit;

an implantable controller unit remote from said at least one implantable stimulating unit;

said controller unit having a power source, data generation means for generating data signals, and first transmission means connected to said power source and said data generation means for transmitting to said at least one stimulating unit high frequency signals comprising a power component derived from said power source and a data component carrying said data signals, and said at least one stimulating unit comprising stimulating means for providing stimulus pulses to said patient, receiving means for receiving said high frequency signals and separating therefrom said power and data components, supply means for receiving said separated power component and storing power from same for powering said at least one stimulating unit, and control means for using said separated data component to control operation of said at least one stimulating unit.

2. The system as described in claim 1, wherein said first transmission means comprises periodic means for periodically transmitting said high frequency signal with at least said power component, whereby power is periodically received and stored by said stimulating unit.

3. The system as described in claim 1, wherein said at least one stimulating unit comprises data means for obtaining second data signals representative of patient cardiac activity, and second transmission means for sending said second data signals to said controller unit; and said controller unit comprises second receiving means for receiving said second data signals.

4. The system as described in claim 3, wherein said at least one stimulating unit comprises power request means for controlling said second transmission means to send request signals requesting power transmission from said controller unit, and said controller unit has power respond means for initiating transmission of a said high frequency signal with said power component in response to receipt of said request signals.

5. The system as described in claim 3, wherein said at least one stimulating unit comprises sensor means for sensing patient parameters and for generating patient parameter data signals to represent said patient parameters.

6. The system as described in claim 1, wherein said controller unit comprises first sensor means for sensing signals representative of patient cardiac activity and for generating first cardiac data representative of said cardiac activity, and said data generation means comprises encoding means for encoding said data signals with said first cardiac data.

7. The system as described in claim 6, wherein said first sensor means further senses signals representative of patient physical activity.

8. The system as described in claim 1, wherein said first transmission means has time means for time separating the transmission of said power and data components.

9. The system as described in claim 1, wherein said first transmission means has converting means for converting power from said power source into a said high frequency signal, and modulation means for modulating said high frequency signal with said data component.

10. An implantable system for delivering stimulus pulses to a plurality of respective locations in a patient, comprising:
an implantable first device having a power source and transmitting means for transmitting high frequency signals carrying power external to said first device; and
a plurality of respective implantable second devices, each positioned at a respective one of said locations, each of said second devices having receiving means for receiving power transmitted by said first device and stimulus means for delivering stimulus pulses to said patient.

11. The system as described in claim 10, wherein said transmitting means has a high frequency signal source and modulating means for modulating said high frequency signals with a power signal.

12. The system as described in claim 11, wherein said first device has data encoding means for encoding data control signals on said high frequency signals, whereby said signals carry a power component and a data component.

13. The system as described in claim 10, wherein each said second device comprises a sensor for sensing patient information, and control means for controlling operation of said second device as a function of said patient information.

14. The system as described in claim 13, wherein each said second device comprises a transmitter for transmitting data representative of said patient information to said first device.

15. The system as described in claim 10, wherein said first device has sensor means for sensing patient data, and data encoding means for encoding said patient data to modulate said high frequency signals with said data.

16. The system as described in claim 10, wherein said first device comprises a power transfer controller for controlling the timing of transmitting said high frequency signals.

17. The system as described in claim 10, wherein each of said second devices comprises circuits for carrying out predetermined functions, and comprising power control means for controlling delivery of power from said receiving means to at least some of said circuits.

18. The system as described in claim 10, wherein each of said second devices has request means for transmitting to said first device a request for transmission of power to it.

19. The system as described in claim 10, wherein each of said second devices comprises circuits for performing plurality of predetermined functions and control means for controlling at least some of said circuits to operate in a power sleep or awake mode, and wherein said first device comprises wake-up means for transmitting an instruction to at least one of said second devices to control said circuits to operate in an awake mode.

20. A method for delivering power to a plurality of devices positioned at respective locations in a patient's body, comprising:
providing an implantable main device having a power source;
generating in said main device high frequency signals encoded with a power component, and transmitting said signals to said plurality of devices.

21. The method as described in claim 20, comprising encoding control data on said high frequency signals, and transmitting said high frequency signals with said control data to at least one of said plurality of devices.

22. The method as described in claim 20, comprising controlling each of said plurality of devices to operate in a sleep or awake mode.

23. The method as described in claim 22, wherein comprising transmitting a signal from one of said plurality of devices to said main device to request a power transmission to it.

24. The method as described in claim 23, comprising transmitting from said main device to at least one of said plurality devices a command to operate in the awake mode.

25. The method as described in claim 20, comprising varying one or more parameters of said high frequency signals, detecting the received signals at a remote device, sending data representative of said received signals from said remote device to said main device, and adjusting said one or more parameters as a function of said representative data.

26. An implantable system having at least one implantable remote unit at a given body site and an implantable main device equipped with a battery power source, said at least one remote unit having receiving means for receiving power from high frequency signals and storage means for storing said received power, said main device having transmitter means for transmitting high frequency signals carrying at least a power component to said remote unit.

27. The system as described in claim 26, wherein said main device has control means for controlling the timing of transmitting said high frequency signals to said at least one remote unit.

28. The system as described in claim 27, wherein said main device has adjust means for adjusting a parameter of said high frequency signals.

29. The system as described in claim 28, comprising a plurality of said remote units, each positioned at a respective given body site.

30. The system as described in claim 29, wherein each said remote unit has data collection means for collecting data representative of its operation, and remote transmission means for transmitting said collected data to said main device, and said control means has means for performing said controlling as a function of said collected data.

31. The system as described in claim 30, wherein said control means has means for performing said adjusting as a function of said collected data.

* * * * *